US009393345B2

(12) United States Patent
Heckroth et al.

(10) Patent No.: US 9,393,345 B2
(45) Date of Patent: Jul. 19, 2016

(54) MEDICAL ADHESIVE FOR STEMMING BLEEDING

(75) Inventors: Heike Heckroth, Odenthal (DE); Christoph Eggert, Köln (DE)

(73) Assignee: Adhesys Medical GmbH, Aachen (DE)

(*) Notice: Subject to any disclaimer, the term of this patent is extended or adjusted under 35 U.S.C. 154(b) by 122 days.

(21) Appl. No.: 14/112,368

(22) PCT Filed: Apr. 17, 2012

(86) PCT No.: PCT/EP2012/057016
§ 371 (c)(1),
(2), (4) Date: Nov. 13, 2013

(87) PCT Pub. No.: WO2012/143356
PCT Pub. Date: Oct. 26, 2012

(65) Prior Publication Data
US 2014/0065091 A1    Mar. 6, 2014

(30) Foreign Application Priority Data
Apr. 19, 2011  (EP) ................... 11162943

(51) Int. Cl.
*C08G 18/10* (2006.01)
*C08G 18/12* (2006.01)
*C08G 18/73* (2006.01)
*A61L 24/04* (2006.01)
*A61L 24/00* (2006.01)

(52) U.S. Cl.
CPC .......... *A61L 24/046* (2013.01); *A61L 24/0015* (2013.01); *C08G 18/10* (2013.01); *C08G 18/12* (2013.01); *C08G 18/73* (2013.01)

(58) Field of Classification Search
None
See application file for complete search history.

(56) References Cited

U.S. PATENT DOCUMENTS

| | | | | |
|---|---|---|---|---|
| 3,479,310 | A * | 11/1969 | Bayer et al. | 524/591 |
| 3,886,122 | A * | 5/1975 | Fabris et al. | 528/53 |
| 4,040,992 | A * | 8/1977 | Bechara et al. | 521/117 |
| 4,190,566 | A * | 2/1980 | Noll et al. | 524/839 |
| 4,334,944 | A * | 6/1982 | Creyf | 156/308.2 |
| 4,501,852 | A * | 2/1985 | Markusch et al. | 524/591 |
| 4,587,149 | A * | 5/1986 | Murachi | 428/90 |
| 5,126,170 | A * | 6/1992 | Zwiener et al. | 427/385.5 |
| 5,236,741 | A * | 8/1993 | Zwiener et al. | 427/385.5 |
| 5,243,012 | A * | 9/1993 | Wicks et al. | 528/58 |
| 5,397,930 | A * | 3/1995 | Nilssen | 307/150 |
| 5,594,097 | A * | 1/1997 | Chaffanjon et al. | 528/419 |
| 5,736,604 | A * | 4/1998 | Luthra | 524/591 |
| 5,925,781 | A * | 7/1999 | Pantone et al. | 560/26 |
| 6,296,607 | B1 * | 10/2001 | Milbocker | 600/30 |
| 6,359,101 | B1 * | 3/2002 | O'Connor et al. | 528/66 |
| 6,458,293 | B1 * | 10/2002 | Roesler et al. | 252/182.23 |
| 6,482,333 | B1 * | 11/2002 | Roesler et al. | 252/182.12 |
| 7,754,782 | B2 * | 7/2010 | Heckroth et al. | 523/111 |
| 8,168,431 | B2 * | 5/2012 | Brady et al. | 435/396 |
| 2003/0135238 | A1 * | 7/2003 | Milbocker | 606/231 |
| 2004/0067315 | A1 * | 4/2004 | Niesten et al. | 427/372.2 |
| 2004/0157945 | A1 * | 8/2004 | Barber | 521/155 |
| 2005/0129733 | A1 * | 6/2005 | Milbocker et al. | 424/423 |
| 2005/0131095 | A1 * | 6/2005 | Yu et al. | 521/159 |
| 2006/0058410 | A1 * | 3/2006 | Yu et al. | 521/155 |
| 2007/0003594 | A1 * | 1/2007 | Brady et al. | 424/426 |
| 2007/0160851 | A1 * | 7/2007 | Barancyk et al. | 428/423.1 |
| 2008/0067720 | A1 * | 3/2008 | Wiese et al. | 264/334 |
| 2008/0145696 | A1 * | 6/2008 | Senkfor et al. | 428/687 |
| 2009/0012206 | A1 * | 1/2009 | Heckroth et al. | 523/111 |
| 2011/0123479 | A1 | 5/2011 | Heckroth et al. | |
| 2011/0294934 | A1 | 12/2011 | Wamprecht et al. | |
| 2012/0178847 | A1 | 7/2012 | Heckroth et al. | |

FOREIGN PATENT DOCUMENTS

| | | |
|---|---|---|
| DE | 102009007194 A1 | 8/2010 |
| EP | 2011808 A1 | 1/2009 |
| EP | 2145634 A1 | 1/2010 |
| EP | 2275466 A1 | 1/2011 |
| WO | WO-2010006714 A2 | 1/2010 |

OTHER PUBLICATIONS

PEG 300, Sigma—Aldrich, downloaded Aug. 10, 2014.*
International Search Report for PCT/EP2012/057016 mailed Jul. 12, 2012.

* cited by examiner

*Primary Examiner* — Peter A Salamon
(74) *Attorney, Agent, or Firm* — Drinker Biddle & Reath LLP

(57) ABSTRACT

The present invention relates to a polyurea system comprising as component A) isocyanate-functional prepolymers obtainable by reaction of aliphatic isocyanates A1) with polyols A2), which in particular can have a number-average molecular weight of ≥400 g/mol and a mean OH functionality of from 2 to 6, as component B) an amino-functional compound of the general formula (I) in which X is an organic radical containing a secondary amino function, Y is an organic radical that contains a tertiary amino group and does not contain Zerewitinoff-active hydrogen, $R_1$ is a $CH_2$—$COOR_3$ radical in which $R_3$ is an organic radical that does not contain Zerewitinoff-active hydrogen, a linear or branched C1- to C4-alkyl radical, a cyclopentyl radical, a cyclohexyl radical or H, $R_2$ is an organic radical that does not contain Zerewitinoff-active hydrogen, a is 1 or 2, b is 1 or 2, and a+b=2 or 3, for stemming the escape of blood, and to a metering system for the polyurea system according to the invention.

16 Claims, No Drawings

MEDICAL ADHESIVE FOR STEMMING BLEEDING

RELATED APPLICATIONS

This application is a national stage application (under 35 U.S.C. §371) of PCT/ET2012/057016, filed Apr. 17, 2012, which claims benefit of European Application No. 11162943.2, Apr. 19, 2011, which is incorporated by reference herein.

The present invention relates to a polyurea system in particular for stemming bleeding, and to a metering system for the polyurea system according to the invention.

Various materials that are used as tissue adhesives are available commercially. They include the cyanoacrylates Dermabond® (octyl 2-cyanoacrylate) and Histoacryl Blue® (butyl cyanoacrylate). However, a prerequisite for efficient bonding of cyanoacrylates is a dry substrate. Such adhesives fail where there is pronounced bleeding.

As an alternative to the cyanoacrylates, biological adhesives such as, for example, BioGlue®, a mixture of glutaraldehyde and bovine serum albumin, various collagen- and gelatin-based systems (FloSeal®) and the fibrin adhesives (Tissucol) are available. Such systems are used primarily for stemming bleeding (haemostasis). In addition to the high costs, fibrin adhesives are distinguished by a relatively weak adhesive strength and rapid degradation, so that they can only be used in the case of relatively small injuries on unstretched tissue. Collagen- and gelatin-based systems such as FloSeal® are used solely for haemostasis. In addition, because fibrin and thrombin are obtained from human material and collagen and gelatin are obtained from animal material, there is always the risk of an infection in biological systems. Biological materials must additionally be stored in cool conditions, so that their use in emergency care, such as, for example, in disaster areas, in military campaigns, etc., is not possible. Traumatic wounds are treated in such cases with QuikClot® or QuikClot ACS+™, which is a mineral granulate that is introduced into the wound in an emergency and, by removing water, leads to coagulation. In the case of QuikClot®, this is a strongly exothermic reaction, which leads to burns. QuikClot ACS+™ is a gauze into which the salt is embedded. The system must be pressed firmly onto the wound in order to stem bleeding.

The preparation and use of polyurea systems as tissue adhesives is known from EP 2 275 466 A1. The systems disclosed therein comprise an amino-functional aspartic acid ester and an isocyanate-functional prepolymer. A tertiary amine is additionally present. This is used to increase the curing speed of the polyurea system, because that is of considerable importance in particular when the system is used to stem bleeding. The described polyurea systems can be used as tissue adhesives for closing wounds in human and animal cell structures. A very good adhesion result can thereby be achieved. However, there is the risk with the systems described in EP 2 275 466 A1 that at least portions of the amines used to accelerate curing may be eluted in the body. This can lead to undesirable biological effects.

WO02010/006714 A1 describes polyurea systems that comprise at least two components. The components are an amino-functional aspartic acid ester and an isocyanate-functional prepolymer. The described 2-component polyurea systems can be used to stem bleeding, it being possible for the flow of blood to be stopped within a period of from one and a half to two minutes. In some injuries, however, it is desirable to be able to stem bleeding within a significantly shorter time in order to reduce the blood loss and increase a patient's chances of survival. At the same time, however, it is important that the polyurea system is still easy to apply for the user, that is to say its processing time is significantly longer than the curing time.

The object of the invention was, therefore, to provide a polyurea system that allows bleeding to be stemmed particularly quickly and with which there is no risk of low molecular weight amines being released.

The object is achieved according to the invention by a polyurea system comprising
- as component A) isocyanate-functional prepolymers obtainable by reaction of
  - aliphatic isocyanates A1) with
  - polyols A2), which in particular can have a number-average molecular weight of ≥400 g/mol and a mean OH functionality of from 2 to 6,
- as component B) an amino-functional compound of the general formula (I)

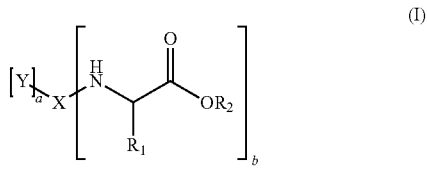

in which
- X is an organic radical containing a secondary amino function,
- Y is an organic radical that contains a tertiary amino group and does not contain Zerewitinoff-active hydrogen,
- $R_1$ is $CH_2$—$COOR_3$ radical in which $R_3$ is an organic radical that does not contain Zerewitinoff-active hydrogen, a linear or branched C1- to C4-alkyl radical, a cyclopentyl radical, a cyclohexyl radical or H,
- $R_2$ is an organic radical that does not contain Zerewitinoff-active hydrogen,
- a is 1 or 2,
- b is 1 or 2,
- and a+b=2 or 3.

The polyurea system according to the invention is distinguished in that it can stop the escape of blood instantaneously even in the presence of large amounts of fluid and nevertheless has a processing time of about 3 minutes. In the presence of small amounts of fluid, the system acts as a tissue adhesive, which both bonds and seals wounds.

Because the system according to the invention also does not contain low molecular weight amines bonded into the polymer network, there is also no risk that such compounds might be eluted and thereby released in the body.

For the definition of Zerewitinoff-active hydrogen, reference is made to Römpp Chemie Lexikon, Georg Thieme Verlag Stuttgart. Groups with Zerewitinoff-active hydrogen are preferably understood as being OH, NH or SH.

According to a preferred form of the polyurea system according to the invention, X is a radical of formula (II)

in which
R$_4$, R$_5$ each independently of one another or simultaneously are an organic radical that does not contain Zerewitinoff-active hydrogen.

It is particularly preferred here if R$_4$, R$_5$ each independently of one another or simultaneously are a linear or branched, saturated organic radical optionally substituted in the chain by heteroatoms, in particular a linear or branched, saturated, aliphatic C1 to C10, preferably C2 to C8, particularly preferably C2 to C6 hydrocarbon radical, and most particularly preferably a methyl, ethyl, propyl or butyl radical.

According to a further preferred embodiment of the invention, it is provided that Y is an organic radical of the general formula (III)

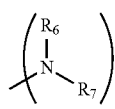

(III)

in which
R$_6$, R$_7$ each independently of one another or simultaneously are an organic radical that does not contain Zerewitinoff-active hydrogen.

Particularly preferably, R$_6$, R$_7$ each independently of one another or simultaneously are a methyl, ethyl or propyl radical.

Also advantageous is a polyurea system comprising a compound of formula (I) in which the radicals R$_1$, R$_2$ and optionally R$_3$ each independently of one another or simultaneously are a linear or branched C1 to C10, preferably C1 to C8, particularly preferably C2 to C6, most particularly preferably C2 to C4 organic radical and in particular an aliphatic hydrocarbon radical. Examples of particularly suitable radicals are methyl, ethyl, propyl and butyl.

The isocyanate-functional prepolymers A) are obtainable by reaction of polyisocyanates A1) with polyols A2), optionally with the addition of catalysts as well as auxiliary substances and additives.

There can be used as the polyisocyanates A1), for example, monomeric aliphatic or cycloaliphatic di- or tri-isocyanates such as 1,4-butylene diisocyanate (BDI), 1,6-hexamethylene diisocyanate (HDI), isophorone diisocyanate (IPDI), 2,2,4- and/or 2,4,4-trimethylhexamethylene diisocyanate, the isomeric bis-(4,4'-isocyanatocyclohexyl)-methanes or mixtures thereof of any desired isomer content, 1,4-cyclohexylene diisocyanate, 4-isocyanatomethyl-1,8-octane diisocyanate (nonane triisocyanate), 2-isocyanatoethyl 6-isocyanatocaproate, as well as alkyl 2,6-diisocyanatohexanoate (lysine diisocyanate) having C1-C8-alkyl groups.

In addition to the monomeric polyisocyanates A1) mentioned above there can also be used the higher molecular weight secondary products thereof having a uretdione, isocyanurate, urethane, allophanate, biuret, iminooxadiazinedione or oxadiazinetrione structure and mixtures thereof.

Preference is given to the use of polyisocyanates A1) of the above-mentioned type having only aliphatically or cycloaliphatically bonded isocyanate groups or mixtures thereof.

It is likewise preferred for polyisocyanates A1) of the above-mentioned type having a mean NCO functionality of from 1.5 to 2.5, preferably of from 1.6 to 2.4, more preferably of from 1.7 to 2.3, most particularly preferably of from 1.8 to 2.2 and in particular of 2 to be used.

Hexamethylene diisocyanate is most particularly preferably used as the polyisocyanate A1).

According to a further preferred form of the polyurea system according to the invention, it is provided that the polyols A2) are polyester polyols and/or polyester-polyether polyols and/or polyether polyols. Particular preference is given to polyester-polyether polyols and/or polyether polyols having an ethylene oxide content of from 60 to 90 wt. %.

It is also preferred for the polyols A2) to have a number-average molecular weight of from 4000 to 8500 g/mol.

Suitable polyether ester polyols are prepared according to the prior art preferably by polycondensation from polycarboxylic acids, anhydrides of polycarboxylic acids and esters of polycarboxylic acids with readily volatile alcohols, preferably C1 to C6 monools, such as methanol, ethanol, propanol or butanol, with low molecular weight and/or higher molecular weight polyol in molar excess; wherein there are used as the polyol ether-group-containing polyols optionally in mixtures with other ether-group-free polyols.

Mixtures of the higher molecular weight and of the low molecular weight polyols can, of course, also be used for the polyether ester synthesis.

Such low molecular weight polyols in molar excess are polyols having molar masses of from 62 to 299 daltons, having from 2 to 12 carbon atoms and hydroxyl functionalities of at least 2, which can further be branched or unbranched and the hydroxyl groups of which are primary or secondary. These low molecular weight polyols can also contain ether groups. Typical representatives are ethylene glycol, 1,2-propanediol, 1,3-propanediol, 1,4-butanediol, 2,3-butanediol, 2-methyl-1,3-propanediol, 1,5-pentanediol, 1,6-hexanediol, 3-methyl-1,5-pentanediol, 1,8-octanediol, 1,10-decanediol, 1,12-dodecanediol, cyclohexanediol, diethylene glycol, triethylene glycol and higher homologues, dipropylene glycol, tripropylene glycol and higher homologues, glycerol, 1,1,1-trimethylolpropane, and oligo-tetrahydrofurans with hydroxyl end groups. Mixtures within this group can, of course, also be used.

Higher molecular weight polyols in molar excess are polyols having molar masses of from 300 to 3000 daltons, which can be obtained by ring-opening polymerisation of epoxides, preferably ethylene oxide and/or propylene oxide, as well as by acid-catalysed, ring-opening polymerisation of tetrahydrofuran. Either alkali hydroxides or double-metal-cyanide catalysts can be used for the ring-opening polymerisation of epoxides.

As starters for ring-opening epoxide polymerisations there can be used all at least bifunctional molecules from the group of the amines and the above-mentioned low molecular weight polyols. Typical representatives are 1,1,1-trimethylolpropane, glycerol, o-TDA, ethylenediamine, 1,2-propylene glycol, etc., as well as water, including mixtures thereof. Mixtures within the group of the excess higher molecular weight polyols can, of course, also be used.

The synthesis of the higher molecular weight polyols, in so far as hydroxyl-group-terminated polyalkylene oxides of ethylene oxide and/or propylene oxide are concerned, can be effected randomly or block-wise, it also being possible for mixed blocks to be present.

Polycarboxylic acids are both aliphatic and aromatic carboxylic acids, which can be both cyclic, linear, branched or unbranched and which can contain from 4 to 24 carbon atoms.

Examples are succinic acid, glutaric acid, adipic acid, azelaic acid, sebacic acid, 1,10-decanedicarboxylic acid, 1,12-dodecanedicarboxylic acid, phthalic acid, terephthalic acid, isophthalic acid, trimellitic acid, pyromellitic acid. Succinic acid, glutaric acid, adipic acid, sebacic acid, lactic acid, phthalic acid, terephthalic acid, isophthalic acid, trimellitic acid, pyromellitic acid are preferred. Succinic acid, glutaric acid and adipic acid are particularly preferred.

The group of the polycarboxylic acids also includes hydroxycarboxylic acids, or their inner anhydrides, such as, for example, caprolactone, lactic acid, hydroxybutyric acid, ricinoleic acid, etc. Also included are monocarboxylic acids, in particular those which have more than 10 carbon atoms, such as soybean oil fatty acid, palm oil fatty acid and groundnut oil fatty acid, wherein the proportion thereof in the whole of the reaction mixture constituting the polyether ester polyol is not more than 10 wt. % and, in addition, the accompanying low functionality is compensated for by the concomitant use of at least trifunctional polyols, whether it be on the side of the low molecular weight or high molecular weight polyols.

The preparation of the polyether ester polyol is preferably carried out according to the prior art at elevated temperature in the range from 120 to 250° C., initially under normal pressure, later with the application of a vacuum of from 1 to 100 mbar, preferably, but not necessarily, using an esterification or transesterification catalyst, the reaction being completed until the acid number falls to values of from 0.05 to 10 mg KOH/g, preferably from 0.1 to 3 mg KOH/g and particularly preferably from 0.15 to 2.5 mg KOH/g.

An inert gas can further be used during the normal pressure phase prior to the application of a vacuum. Of course, liquid or gaseous entrainers can also be used as an alternative or for individual phases of the esterification. For example, the water of reaction can be discharged equally as well when nitrogen is used as carrier gas as when an azeotropic entrainer, such as, for example, benzene, toluene, xylene, dioxane, etc., is used.

Mixtures of polyether polyols with polyester polyols in arbitrary ratios can, of course, also be used.

Polyether polyols are preferably polyalkylene oxide polyethers based on ethylene oxide and optionally propylene oxide.

Such polyether polyols are preferably based on difunctional or higher functional starter molecules such as difunctional or higher functional alcohols or amines.

Examples of such starters are water (regarded as a diol), ethylene glycol, propylene glycol, butylene glycol, glycerol, TMP, sorbitol, pentaerythritol, triethanolamine, ammonia or ethylenediamine.

Hydroxyl-group-containing polycarbonates, preferably polycarbonate diols, having number-average molecular weights $M_n$ of from 400 to 8000 g/mol, preferably from 600 to 3000 g/mol, can likewise be used. They are obtainable by reaction of carbonic acid derivatives, such as diphenyl carbonate, dimethyl carbonate or phosgene, with polyols, preferably diols.

Examples of such diols are ethylene glycol, 1,2- and 1,3-propanediol, 1,3- and 1,4-butanediol, 1,6-hexanediol, 1,8-octanediol, neopentyl glycol, 1,4-bishydroxymethylcyclohexane, 2-methyl-1,3-propanediol, 2,2,4-trimethyl-1,3-pentanediol, dipropylene glycol, polypropylene glycols, dibutylene glycol, polybutylene glycols, bisphenol A and lactone-modified diols of the above-mentioned type.

For the preparation of the prepolymer A), the polyisocyanate A1) can be reacted with the polyol A2) with an NCO/OH ratio of preferably from 4:1 to 12:1, particularly preferably 8:1, and then the content of unreacted polyisocyanate can be separated off by suitable methods. Thin-film distillation is conventionally used for that purpose, there being obtained prepolymers having residual monomer contents of less than 1 wt. %, preferably less than 0.1 wt. %, most particularly preferably less than 0.03 wt. %.

During the preparation, stabilisers such as benzoyl chloride, isophthaloyl chloride, dibutyl phosphate, 3-chloropropionic acid or methyl tosylate can optionally be added.

The reaction temperature in the preparation of the prepolymers A) is preferably from 20 to 120° C. and more preferably from 60 to 100° C.

The prepolymers that are prepared have a mean NCO content, measured in accordance with DIN EN ISO 11909, of from 2 to 10 wt. %, preferably from 2.5 to 8 wt. %.

According to a further form of the polyurea system according to the invention, the prepolymers A) can have a mean NCO functionality of from 1.5 to 2.5, preferably of from 1.6 to 2.4, more preferably of from 1.7 to 2.3, most particularly preferably of from 1.8 to 2.2 and in particular of 2.

In a further development of the invention it is provided that the polyurea system additionally comprises organic fillers C). These can in particular have a viscosity at 23° C., measured in accordance with DIN 53019, in the range of from 10 to 20,000 mPas, preferably from 50 to 4000 mPas and particularly preferably from 50 to 2000 mPas.

The organic fillers of component C) can preferably be hydroxy-functional compounds, in particular polyether polyols.

It is also advantageous for the fillers of component C) to have a mean OH functionality of from 1.5 to 3, preferably of from 1.8 to 2.2 and particularly preferably of 2.

For example, there can be used as organic fillers C) polyethylene glycols that are liquid at 23° C., such as PEG 200 to PEG 600, their mono- or di-alkyl ethers such as PEG 500 dimethyl ether, liquid polyether and polyester polyols, liquid polyesters such as, for example, Ultramoll (Lanxess AG, Leverkusen, DE), and glycerol and its liquid derivatives such as, for example, triacetin (Lanxess AG, Leverkusen, DE).

In a further preferred form of the polyurea system according to the invention, polyethylene glycols are used as organic fillers. They preferably have a number-average molecular weight of from 100 to 1000 g/mol, particularly preferably from 200 to 400 g/mol.

In order further to reduce the mean equivalent weight of the compounds used overall for the prepolymer crosslinking, based on the NCO-reactive groups, it is additionally possible to prepare reaction products of the prepolymers A) with the amino-functional compound B) and/or the organic fillers C), provided they are amino- or hydroxy-functional, in a separate preliminary reaction and then use them as the higher molecular weight curing agent component.

Preferably, ratios of isocyanate-reactive groups to isocyanate groups of from 50 to 1 to 1.5 to 1, particularly preferably from 15 to 1 to 4 to 1, are established in the pre-extension.

The advantage of this modification by pre-extension is that the equivalent weight and the equivalent volume of the curing agent component can be modified within wider limits. Commercially available 2-chamber metering systems can accordingly be used for the application, in order to obtain a system which, with existing chamber volume ratios, can be adjusted to the desired ratio of NCO-reactive groups to NCO groups.

It is, of course, also possible to incorporate into the polyurea systems as component D) pharmacologically active ingredients such as analgesics with and without anti-inflammatory activity, antiphlogistics, substances having antimicrobial activity, antimycotics, substances having antiparasitic activity.

The polyurea system according to the invention can be obtained by mixing the prepolymers A) with the amino-functional compound B) and optionally components C) and D). The ratio of free or blocked amino groups to free NCO groups is preferably 1:1.5, particularly preferably 1:1.

The polyurea system according to the invention is suitable in particular for sealing, bonding, gluing or covering cell tissue and in particular for stemming the escape of blood or tissue fluids or for sealing leaks in cell tissue. Most particularly preferably, it can as such be used for this purpose or it can be used for the production of an agent for stemming bleeding and/or for sealing blood vessels. By means of the polyurea system according to the invention it is possible to produce fluid-tight, rapidly curing, transparent, flexible and biocompatible seams which adhere firmly to the tissue.

The invention further provides a metering system having two chambers for a polyurea system according to the invention, in which one chamber contains component A) and the other chamber contains component B) and optionally components C) and. D) of the polyurea system. Such a metering system is suitable in particular for applying the polyurea system to tissue.

The invention will be explained in greater detail below by means of examples.

EXAMPLES

Methods:

Molecular weights were determined by means of gel permeation chromatography (GPC) as follows: Calibration is carried out using polystyrene standards with molecular weights of Mp 1,000,000 to 162. Tetrahydrofuran p.A. was used as eluant. The following parameters were observed during the double measurement: degassing: online degasser; flow rate: 1 ml/min; analysis time: 45 minutes; detectors: refractometer and UV detector; injection volume: 100 μl-200 μl. Calculation of the molar mass means Mw; Mn and Mp and of the polydispersity Mw/Mn was carried out with software assistance. Baseline points and evaluation limits were fixed in accordance with DIN 55672 Part 1.

NCO contents were determined volumetrically in accordance with DIN-EN ISO 11909, unless expressly mentioned otherwise.

Viscosities were determined in accordance with ISO 3219 at 23° C.

Residual monomer contents were determined in accordance with DIN ISO 17025.

NMR spectra were determined using a Bruker DRX 400 device.

Substances:

HDI: hexamethylene diisocyanate (Bayer MaterialScience AG)

All other chemicals were acquired from Aldrich and Fluka.

Prepolymer A 465 g of HDI and 2.35 g of benzoyl chloride were placed in a one-litre four-necked flask. Within a period of 2 hours, 931.8 g of a polyether having an ethylene oxide content of 71% and a propylene oxide content of 29% (in each case based on the total alkylene oxide content), started on glycerol, were added at 80° C., and stirring was then carried out for one hour. Excess HDI was then distilled off by thin-film distillation at 130° C. and 0.13 mbar. 980 g (71%) of the prepolymer having an NCO content of 2.53% were obtained. The residual monomer content was <0.03% HDI.

Diethyl N-(3-{[3-(dimethylamino)propyl]amino}propyl) aspartate (1)

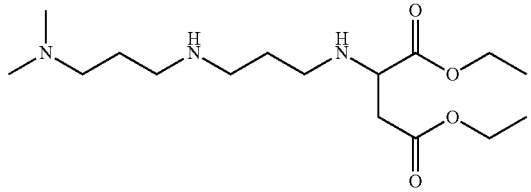 [SMILES: CCOC(=O)CC(NCCCNCCCN(C)C)C(=O)OCC]

10.33 g (0.06 mol) of diethyl maleate were added dropwise to 9.6 g (0.06 mol) of N,N'-dimethyldipropylenetriamine. The reaction mixture was then heated for three days at 60° C. until no further diethyl maleate could be detected in the reaction mixture. The product was obtained quantitatively in the form of a yellow liquid.

$^1$H-NMR (CDCl$_3$, 400 MHz): δ=1.26 (t, 3H), 1.30 (t, 3H), 1.67 (m, 4H), 2.20 (s, 6H), 2.30 (dd, 2H), 2.67 (m, 8H), 3.61 (t, 1H), 4.15 (q, 2H), 4.20 (q, 2H).

$^{13}$C-NMR (CDCl$_3$, 400 MHz): 14.5, 18.5, 28.2, 30.3, 38.1, 45.8, 46.5, 48.2, 49.6, 57.5, 58.0, 59.7, 60.6, 171.2, 173.6.

Tetraethyl 2,2'-[(2-methylpentane-1,5-diyl)diimino]dibutanedioate (2)

1 mol of 2-methyl-1,5-diaminopentane was slowly added dropwise, under a nitrogen atmosphere, to 2 mol of diethyl maleate, in such a manner that the reaction temperature did not exceed 60° C. Heating was then carried out at 60° C. until no further diethyl maleate could be detected in the reaction mixture. The product was obtained quantitatively in the form of a yellow liquid.

Production of the Tissue Adhesive 4 g of prepolymer A were stirred thoroughly in a beaker with an equivalent amount of 1. Immediately thereafter, the polyurea system was applied as a thin layer to the muscle tissue to be bonded. The processing time was 2 min 50 s. The time for which the polyurea system had a sufficiently low viscosity that it could be applied to the tissue without difficulty was determined as the processing time.

In addition, the adhesive force was determined by coating two pieces of muscle tissue (1=4 cm, h=0.3 cm, b=1 cm) with the polyurea system 1 cm from the ends and adhesively bonding them so that they overlapped. The adhesive force of the polyurea system was tested after 2 minutes by pulling. Strong adhesion has occurred.

In Vitro Haemostasis Test

In order to study the haemostatic activity, a piece of muscle tissue about 5×10 cm in size and 1 cm thick was clamped in a device consisting of three clamps fastened to a stand rod. While the adhesive was being applied, water was pumped into the tissue from beneath by means of a 100 ml syringe, so that the water spurted upwards out of the tissue. The time after which no further fluid escaped from the surface of the piece of tissue was measured. When the polyurea system according to the invention was used, this was the case after about 5-10 seconds, that is to say a layer had formed within that time which prevented any further fluid from escaping from the tissue surface. Instead, the fluid escaped from the tissue edges that were not coated with polyurea and ran downwards. It was not possible to detach the adhesive without damaging the muscle tissue.

Comparison Example Haemostasis Test

For comparison purposes, prepolymer A was mixed with an equivalent amount of tetraethyl 2,2'-[(2-methylpentane-1, 5-diyl)diimino]dibutanedioate and tested on the muscle tissue in the same manner. Sealing of the tissue did not occur until after about one and a half minutes in this case.

The above tests clearly show that the polyurea system according to the invention is suitable for stemming bleeding particularly quickly.

The invention claimed is:

1. A method for stemming the escape of blood or tissue fluids comprising preparing a polyurea system comprising
as component A) an isocyanate-functional prepolymer obtained by reacting
an aliphatic isocyanate A1) with a
polyol A2), which in particular can have a number-average molecular weight of ≥400 g/mol and a mean OH functionality of from 2 to 6, and
as component B) an amino-functional compound of the general formula (I)

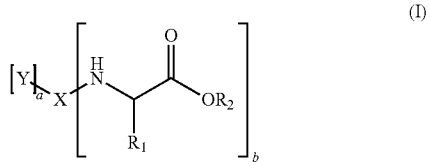

in which
X is an organic radical containing a secondary amino function,
Y is an organic radical that contains a tertiary amino group and does not contain Zerewitinoff-active hydrogen,
$R_1$ is a $CH_2$—$COOR_3$ radical in which $R_3$ is an organic radical that does not contain Zerewitinoff-active hydrogen, and is a linear or branched C1- to C4-alkyl radical, a cyclopentyl radical, a cyclohexyl radical or H,
$R_2$ is an organic radical that does not contain Zerewitinoff-active hydrogen,
a is 1 or 2,
b is 1 or 2,
and a +b =2 or 3, wherein the polyurea system does not contain low molecular weight amines, and
applying the polyurea system to a tissue thereby stemming the escape of blood or tissue fluid.

2. The method according to claim 1, wherein X is a radical of formula (II)

in which
$R_4$, $R_5$ each independently of one another or simultaneously are an organic radical that does not have Zerewitinoff-active hydrogen.

3. The method according to claim 2, wherein $R_4$, $R_5$ each independently of one another or simultaneously are a linear or branched, saturated organic radical optionally substituted in the chain by hetero atoms.

4. The method according to claim 1, wherein Y is an organic radical of the general formula (III)

in which
$R_6$, $R_7$ each independently of one another or simultaneously are an organic radical that does not contain Zerewitinoff-active hydrogen.

5. The method according to claim 4, wherein $R_6$, $R_7$ each independently of one another or simultaneously are a methyl, ethyl or propyl radical.

6. The method according to claim 1, wherein $R_1$, $R_2$ and optionally $R_3$ each independently of one another or simultaneously are a linear or branched C 1 to C10.

7. The method according to claim 1, wherein the polyol A2) comprises a polyester polyol and/or a polyester-polyether polyol and/or a polyether polyol, and in particular a polyester-polyether polyol and/or a polyether polyol having an ethylene oxide content of from 60 to 90 wt.%.

8. The method according to claim 1, wherein the polyol A2) has a number-average molecular weight of from 4000 to 8500 g/mol.

9. The method according to claim 1, comprising as component C) an organic filler which in particular can have a viscosity at 23° C., measured in accordance with DIN 53019, in the range of from 10 to 20,000 mPas.

10. The method according to claim 9, wherein the organic filler is a hydroxy-functional compound.

11. The method according to claim 10, wherein the hydroxy-functional compound is a polyether polyol.

12. The method according to claim 10, wherein the hydroxy-functional compound has a mean OH functionality of from 1.5 to 3.

13. The method according to claim 1, comprising as component D) a pharmacologically active compound, in particular analgesics with or without anti-inflammatory activity, antiphlogistics, substances having antimicrobial activity, or antimycotics.

14. The method according to claim 1, wherein the polyurea system is applied with a metering system, wherein the metering system comprises two chambers for the polyurea system wherein one of the chamber comprises component A) and the other chamber comprises component B) and optionally components C) and D).

15. The method according to claim 1, wherein $R_1$, $R_2$ and optionally $R_3$ each independently of one another or simultaneously are a linear or branched C1 to C10,
wherein X is a radical of formula (II)

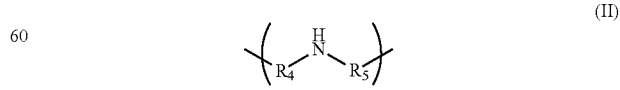

in which
$R_4$, $R_5$ each independently of one another or simultaneously are a linear or branched, saturated organic radical optionally substituted in the chain by hetero atoms wherein Y is an organic radical of the general formula (III)

(III)

in which
R$_6$, R$_7$ each independently of one another or simultaneously are a methyl, ethyl or propyl radical, and
comprising as component C) an organic filler which in particular can have a viscosity at 23° C., measured in accordance with DIN 53019, in the range of from 10 to 20,000 mPas.

16. The method according to claim 1, wherein component B) is diethyl N-(3-{[3-(dimethylamino)propyl]amino}propyl)aspartate.

* * * * *